United States Patent
Faurie

(10) Patent No.: US 11,559,331 B2
(45) Date of Patent: Jan. 24, 2023

(54) ASSEMBLY FOR PLACEMENT OF A CARDIAC, AORTIC OR ARTERIAL IMPLANT WITH STIMULATION ASSISTANCE BY A PERIPHERAL VENOUS OR ARTERIAL CATHETER

(71) Applicant: ELECTRODUCER, Grenoble (FR)

(72) Inventor: Benjamin Faurie, Grenoble (FR)

(73) Assignee: ELECTRODUCER, Grenoble (FR)

( * ) Notice: Subject to any disclaimer, the term of this patent is extended or adjusted under 35 U.S.C. 154(b) by 122 days.

(21) Appl. No.: 17/040,861

(22) PCT Filed: Mar. 29, 2019

(86) PCT No.: PCT/EP2019/058038
§ 371 (c)(1),
(2) Date: Sep. 23, 2020

(87) PCT Pub. No.: WO2019/185880
PCT Pub. Date: Oct. 3, 2019

(65) Prior Publication Data
US 2021/0030440 A1    Feb. 4, 2021

(30) Foreign Application Priority Data

Mar. 29, 2018  (FR) ...................................... 1852770
May 2, 2018   (FR) ...................................... 1853783

(51) Int. Cl.
*A61B 17/34*    (2006.01)
*A61B 17/00*    (2006.01)
(Continued)

(52) U.S. Cl.
CPC .... *A61B 17/3468* (2013.01); *A61B 17/00234* (2013.01); *A61B 17/22* (2013.01);
(Continued)

(58) Field of Classification Search
CPC .............. A61B 17/00234; A61B 17/22; A61B 17/3468; A61B 2017/00044;
(Continued)

(56) References Cited

U.S. PATENT DOCUMENTS 5,370,685 A  12/1994 Stevens
5,545,214 A   8/1996 Stevens
(Continued)

FOREIGN PATENT DOCUMENTS

FR    3034650 A1   10/2016
WO   93/01768 A1    2/1993
(Continued)

OTHER PUBLICATIONS

International Search Report corresponding to International Application No. PCT/EP2019/058038 dated Jun. 3, 2019, 6 pages.
(Continued)

*Primary Examiner* — Mohamed G Gabr
(74) *Attorney, Agent, or Firm* — Ronald M. Kachmarik; Cooper Legal Group LLC

(57) ABSTRACT

An assembly for placement of a cardiac, aortic or arterial implant. The assembly includes an insertion sheath of an introducer or of a delivery catheter, which is of a size smaller than that of an introducer, intended to be introduced into an artery of a human body. The metal support of an electrode of the external cardiac stimulator being integrated into the insertion sheath of a peripheral venous or arterial accessory catheter, or a sleeve around the accessory catheter, which is introduced into the peripheral vein or artery of a patient. The sheath of the accessory catheter or the sleeve is therefore directly in contact with a peripheral vein or artery of the patient.

12 Claims, 5 Drawing Sheets

(51) Int. Cl.
  *A61B 17/22* (2006.01)
  *A61N 1/362* (2006.01)
(52) U.S. Cl.
  CPC .... *A61N 1/362* (2013.01); *A61B 2017/00243* (2013.01); *A61B 2017/00292* (2013.01); *A61B 2017/22097* (2013.01)
(58) Field of Classification Search
  CPC ........... A61B 2017/00243; A61B 2017/00292; A61B 2017/22097; A61F 2/2436; A61N 1/056; A61N 1/362; A61N 1/3625
  See application file for complete search history.

(56) References Cited

U.S. PATENT DOCUMENTS

| | | | |
|---|---|---|---|
| 5,733,323 | A | 3/1998 | Buck et al. |
| 5,814,097 | A | 9/1998 | Sterman et al. |
| 7,018,406 | B2 | 3/2006 | Seguin |
| 7,892,281 | B2 | 2/2011 | Seguin |
| 8,652,202 | B2 | 2/2014 | Alon et al. |
| 8,747,459 | B2 | 6/2014 | Nguyen et al. |
| 2003/0078623 | A1* | 4/2003 | Weinberg ........... A61N 1/36114 607/9 |
| 2009/0270941 | A1 | 10/2009 | Mokelke et al. |
| 2009/0318993 | A1* | 12/2009 | Eidenschink .. A61B 17/320725 607/10 |
| 2011/0040344 | A1 | 2/2011 | Mokelke et al. |
| 2013/0096555 | A1 | 4/2013 | Krom |
| 2018/0071092 | A1* | 3/2018 | Faurie ................ A61B 17/3468 |
| 2019/0224011 | A1* | 7/2019 | Faurie .................... A61B 18/16 |

FOREIGN PATENT DOCUMENTS

| | | |
|---|---|---|
| WO | 97/28807 A1 | 8/1997 |
| WO | 2016/162315 A1 | 10/2016 |

OTHER PUBLICATIONS

Gilard, et al, "Registry of Transcatheter Aortic-Valve Implantation in High-Risk Patients"; the New England Journal of Medicine: pp. 1705-1715.

Susanne Navarini, et al, "Left Ventricular Guidewire Pacing to Simplify Aortic Balloon Valvuloplasty"; Catheterization and Cardiovascular Interventions 73: pp. 426-427 (2009).

Roland Prodzinsky, et al, "A novel Approach for Transcoronary Pacing in a Porcine Model"; Journal of Invasive Cardiology 24(9): pp. 451-455 (2012).

Konstantin M. Heinroth, et al, "Optimizing of Transcoronary Pacing in a Porcine Model"; Journal of Invasive Cardiology 21, pp. 634-638 (2009).

* cited by examiner

ASSEMBLY FOR PLACEMENT OF A CARDIAC, AORTIC OR ARTERIAL IMPLANT WITH STIMULATION ASSISTANCE BY A PERIPHERAL VENOUS OR ARTERIAL CATHETER

TECHNICAL FIELD

The present invention relates to an assembly for placement of a cardiac, aortic or arterial implant.

A "cardiac or aortic implant" is understood here, and in the context of the invention, as a prosthetic cardiac or aortic valve intended for the replacement of a native valve.

A preferred use is the replacement of a cardiac valve by a percutaneous route, comprising a valve delivery catheter and optionally an insertion device, commonly called an "introducer".

An operation for replacement of a cardiac valve by a percutaneous route is usually known by the abbreviation TAVI (transcatheter aortic valve implantation).

Although described with reference to the replacement of an aortic valve, the assembly according to the invention can equally be used for the replacement of another valve of the heart, for example the tricuspid valve or the mitral valve.

An "arterial implant" is understood here, and in the context of the invention, as a prosthetic device which can be a support (balloon, stent) intended to be implanted in an artery of a human being in order to repair (dilate, re-open) a damaged artery.

The invention applies to all types of peripheral vascular interventions on the peripheral arteries, for example the carotid arteries, the aortas, in particular the operations for placement of thoracic aortic endoprostheses (thoracic endovascular aortic repair, or TEVAR) and for placement of carotid stents in persons suffering from narrowing of these arteries (carotid artery stenting, or CAS). These can be cardiac or peripheral interventions performed in pediatrics, particularly in cases of congenital heart disease.

The present invention relates more particularly to improved assistance in the placement by cardiac shutdown by means of a cardiac stimulator, in order to stabilize, secure and optimize the precision of the placement of the various known devices such as stents, balloons or other prostheses.

Generally, the introducer and/or the delivery catheter of the assembly according to the invention can be implanted in a patient by a percutaneous route, more precisely by a transfemoral, transaortic, carotid or subclavian route, or in the peripheral arteries such as the radial or cubital arteries.

PRIOR ART

A commonly known disease of the heart is that associated with calcified narrowing of the cardiac aortic valve, the latter being the valve which separates a cavity of the heart, namely the left ventricle, from the aorta and which, in the open position, allows the blood to flow from the heart to the rest of the body of a human being.

Severe or very severe narrowing prevents the aortic valve from opening normally and thus generates the disease also referred to as calcified aortic valve stenosis.

Treatment of this disease involves replacing the defective aortic valve.

Replacement of a defective aortic valve is most commonly performed by opening the chest, placing the patient under extracorporeal circulation, temporarily stopping the heart, and then opening the heart with the aim of removing the native valve and replacing the latter with an artificial or prosthetic valve.

These successive steps of the operation have the major disadvantages of entailing a relatively long period of hospitalization of the patient, of being complex and costly, and of being limited to only some of the patients affected, since the physician and/or surgeon often considers that so-called "open heart" surgery cannot be performed because it is too risky in light of the general state of the patient, especially on account of the heart having to be stopped and of extracorporeal circulation having to be provided.

To overcome this disadvantage, it has been proposed to replace a cardiac valve using a minimally invasive approach, but still requiring extracorporeal circulation. Mention may be made here of the international patent applications WO 93/01768 and WO 97/28807, and of the U.S. Pat. Nos. 5,814,097, 5,370,685 or 5,545,214, which illustrate known minimally invasive techniques and also instruments for implementing these techniques.

However, it has been felt that the existing techniques are not entirely satisfactory and that they may be improved.

In particular, these techniques have the following major disadvantages:
- they always require the patient to be placed under extracorporeal circulation; they are difficult to implement in practice;
- they do not permit precise control of the diameter by which the native valve is cut, with a view to subsequent calibration of the prosthetic valve;
- they entail risks of diffusion of fragments of the often calcified native valve within the body, which may lead to an embolism;
- they entail risks of perforating the wall of the aorta or heart;
- they entail risks of acute regurgitation of blood during the ablation of the native valve.

To overcome the drawbacks of these techniques, one approach has been the placement of artificial aortic valves, called percutaneous valves, inspired by the techniques of endovascular treatment that involve introduction of a catheter inside a blood vessel, such as the aorta.

Thus, the native aortic valve, which has been rendered defective by calcification, is replaced by an artificial valve without the need for the onerous heart surgery that is normally required as has been explained above.

An artificial valve can currently be put into place by different percutaneous routes: a transfemoral route, i.e. by introduction from the femoral artery to the heart, or a transapical route, or a transaortic route, or a carotid route, or else a subclavian route, that is to say any route that does not require open heart surgery through an opening in the chest and that does not require extracorporeal circulation.

The operation itself involves placing an artificial valve (prosthesis), which reproduces the general shape of a normal native aortic valve, at the region of the calcified (diseased) native aortic valve, the latter being left in place and crushed by the prosthesis.

To do this, the artificial valve made of pericardium, a fine membrane surrounding the heart, of porcine or bovine origin, is fixed beforehand to the interior of a tubular and radially expansible metal mesh, called a stent, which is composed of an arrangement of wires made of shape-memory material, for example nickel-titanium alloy or cobalt-chromium alloy, or stainless steel 316L for coronary stents.

The assembly composed of valve and mesh is then compressed at the end of a tubular sheath, called a delivery catheter, which can be introduced either directly into an artery or into the inside of an introducer permitting access to the artery while maintaining hemostasis.

An interventionalist then slides the assembly composed of valve and mesh into the introducer or directly into the delivery catheter until said assembly arrives at the diseased aortic valve. Before being put in place, the assembly composed of valve and mesh is then placed at the region of the diseased valve by dilation of a balloon.

There are also valve delivery catheters comprising an assembly composed of valve and mesh without a balloon, in which catheters the valve is self-expanding, permitting placement of a valve which expands radially by simple retraction of the sheath surrounding it, and therefore without having to dilate a balloon beforehand.

For further details, reference may be made to the U.S. Pat. Nos. 7,018,406, 7,892,281, 8,652,202 and 8,747,459.

During the placement proper, it is necessary to temporarily arrest the heart for a short period by rapid ventricular stimulation in order to minimize the flow across the valve, i.e. between valvules, and to avoid or at least reduce the potential embolization.

This temporary arrest of the heart, also commonly referred to as "cardiac shutdown", thus involves having the heart beat at 150 to 200 beats per minute such that there is no longer any effective contraction, which leads to a drop in the pressures and simulates ventricular tachycardia or fibrillation and then stabilization of the heart.

This stabilization of the heart permits the stabilization of the balloon and thus increases the precision of placement of the artificial valve in a matter of a few seconds.

There are bipolar stimulation catheters, with two electrodes, referred to as electrosystolic stimulation probes, for temporary intracardiac stimulation of the right ventricle.

These electrosystolic stimulation probes have a number of disadvantages, as are set out below.

Firstly, such a probe constitutes a central venous access with an added risk of vascular complication in the targeted population of patients. The French registry "France 2", which lists the aortic valve replacement operations, currently designated by the English language acronym TAVI (transcatheter aortic valve implantation), has indicated a rate of risk of substantial vascular complications equal to 4.7%. This result is reported on page 1709 of publication [1].

Secondly, this probe is relatively rigid. Hence, its placement in the right ventricle, which is fragile and whose wall is finer than that of the left ventricle, poses a considerable risk of the phenomenon well known to interventionalists under the term "tamponade" which is a manifestation of substantial circulatory insufficiency, which may even lead to the death of the patient.

It should also be noted that this risk exists both during the intervention, that is to say during the placement of the electrosystolic probe, and also in the post-operative period, on account of the mobilization of the patients in their beds and therefore of the probe which is still present and which may then pierce the wall of the right ventricle.

Moreover, there is a risk of the electrosystolic stimulation probe moving at the crucial moment of placement of the valve. This is because a stimulation probe is not fixed in a wall of the heart and may therefore move and thus generate a loss of capture of the electrical stimulation signal.

The heart is then no longer stimulated and therefore performs substantial movements, which impede the placement of the valve or of the balloon.

Another risk associated with the use of such probes is the risk of infection at the puncture site. The registry France 2 has indicated a rate of less than 1%: see publication [1].

Finally, an interventionalist does not consider as negligible the additional operating time associated with the placement of a temporary stimulation probe, which is an operation that is not always easy to perform.

Publication [2] puts forward the advantages of performing this ventricular stimulation on the left ventricle and not on the right ventricle and of doing so not by means of a specific transvenous stimulation catheter but by using an external cardiac stimulator with the guidewire used for interventions of this type.

Thus, the recommended technique described in publication [2] involves using the guidewire which supports the stent expansion balloon and is introduced into the left ventricle, as a part connected to the cathode of a cardiac stimulator, and a cutaneous electrode or needle inserted in the subcutaneous tissue as a support for the anode of the cardiac stimulator.

Publications [3] and [4], in the case of a coronary angioplasty intervention on a pig population, validates the efficacy of temporary cardiac stimulation with a lower stimulation voltage, in which the guidewire supporting the stent expansion balloon is used as a part connected to the cathode of a cardiac stimulator, and a cutaneous electrode or needle inserted in the subcutaneous tissue is used as a support for the anode of the cardiac stimulator.

Thus, these recommended techniques have the advantages of avoiding the need to implant an additional dedicated catheter, of avoiding an additional access to the heart, of reducing the time and cost of the operation, but also of reducing the rate of complications associated with the implantation of the dedicated catheter, all of this while permitting a stimulation that is equal to that achieved by transvenous stimulation.

Moreover, compared to the electrosystolic stimulation probes for the right ventricle, which pose the risk of tamponade as explained above, the guidewire used for this technique is very stable and bears permanently against the relatively thick wall of the left ventricle, since it serves as a rail for advancing the stent/balloon/valve assembly through the valve.

While this is the case, this technique nonetheless requires the placement of an additional electrode or subcutaneous needle, which has to be precise, and the placement and retention of crocodile clips on two supports spaced apart from each other.

The inventor of the present invention has filed the patent application WO2016/162315 A1 which describes and claims the integration of a cardiac stimulator electrode directly in the insertion sheath (introducer or delivery catheter) in the artery of a patient. The proposed invention makes the placement and manipulation of the cardiac stimulator electrodes quicker and easier for the surgeon(s) in charge of the operation.

The disadvantage of the above application is that it requires the production of specific introducers or delivery catheters.

Now, it would be useful to have one or more solutions making it possible to retain existing introducers or catheters, that is to say those that do not have an electrode integrated in them.

More generally, it would be useful if the one or more solutions found applied not only to operations for replacement of a cardiac or aortic valve but also to all operations involving implantation during peripheral vascular interventions.

The object of the invention is to respond at least in part to said need(s).

SUMMARY OF THE INVENTION

To do this, the invention relates, according to a first alternative, to an assembly for replacement of a cardiac valve by a percutaneous route, comprising:

- a device forming an introducer or a valve delivery catheter comprising at least one tubular insertion sheath, intended to be introduced into an artery of a human body and optionally to permit the passage of a surgical intervention device;
- an accessory catheter, intended to be introduced into a peripheral vein or artery of the human body;
- a sleeve adapted to be engaged around the accessory catheter, the sleeve being mad of electrically conductive material over at least part of its outer periphery, such that, when the accessory catheter is introduced into the artery or into the peripheral vein of the human body, the conductive periphery of the sleeve is in contact with the subcutaneous tissue of the body or with the wall of the artery or of the vein, the sleeve additionally comprising an electrical connection to an electrode of a cardiac stimulator outside the body;
- a guidewire intended to be introduced into the tubular sheath of the introducer or of the delivery catheter for advancing the implant, the guidewire comprising a metal part additionally serving as a connection to the other electrode of the external cardiac stimulator.

According to an alternative embodiment, the electrode of the cardiac stimulator connected to the electrically conductive sleeve engaged around the insertion sheath of the accessory catheter is the anode, while the one connected to the metal part of the guidewire introduced into the introducer or the delivery catheter is the cathode.

Advantageously, the electrically conductive sleeve is formed as a single piece made of conductive material, for example carbon.

The sleeve can thus be formed by a sheath comprising on its outer periphery an electrically conductive coating, for example a coating of carbon.

According to an advantageous embodiment, the sleeve is elastic so as to be able to engage on peripheral venous or arterial catheter sheaths of different diameters, typically external diameters of between 0.2 and 2.2 mm.

The invention relates, according to a second alternative, to an assembly for placement of a cardiac, aortic or arterial implant, comprising:

- a device forming an introducer or a valve delivery catheter comprising at least one tubular insertion sheath, intended to be introduced into an artery of a human body and optionally to permit the passage of a surgical intervention device;
- an accessory catheter, intended to be introduced into a peripheral vein or artery of the human body, the accessory catheter comprising at least one tubular insertion sheath and at least one electrically conductive element, of which a distal portion is exposed on at least one part of the outer periphery of the sheath in such a way as to be in contact with the subcutaneous tissue of the body or with the peripheral vein or artery, and of which a proximal portion, accessible from the outside of the body, comprises an electrical connection so as to serve as a connection to an electrode of a cardiac stimulator outside the body;
- a guidewire intended to be introduced into the tubular sheath of the introducer or of the delivery catheter for advancing the implant, the guidewire comprising a metal part additionally serving as a connection to the other electrode of the external cardiac stimulator.

It will be noted here that an "accessory catheter", which can be designated as an ancillary catheter, is a catheter introduced into a peripheral vein or artery, also called the accessory route or else the secondary route or ancillary route.

According to one embodiment, the electrode of the cardiac stimulator connected to the accessory catheter is the anode, while the one connected to the metal part of the guidewire inserted into the introducer or the delivery catheter is the cathode.

Preferably, the electrically conductive element of the accessory catheter is a wire or a metal band housed at least partially within the thickness of the sheath, of which a distal portion is exposed at the outer periphery of the sheath.

The cross section of the wire or of the metal band can advantageously be between 0.25 and 5 mm$^2$.

The assembly according to the invention can constitute an assembly for replacement of a cardiac valve by a percutaneous route, the guidewire being adapted for the advance of an artificial valve intended to replace the cardiac valve.

It can also constitute an assembly for placement of an aortic endoprosthesis or carotid stent, the guidewire being adapted for the advance of the endoprosthesis or stent, or the guidewire being independent of the one which delivers the prosthesis or the balloon but which is coupled to another guidewire in contact with the patient's heart.

By virtue of the peripheral venous catheter according to the invention, which integrates an electrically conductive element at the periphery of its sheath, it is no longer necessary to place a needle in the subcutaneous tissues or a cutaneous electrode to serve as a support for the electrode, typically the anode of a cardiac stimulator.

It is also no longer necessary to use and put in place an electrosystolic probe as in the prior art, commonly called a temporary probe.

Moreover, by virtue of the invention, the stimulation intensity necessary for the cardiac shutdown is lower than in the solutions according to the prior art, on account of a lower impedance of the vascular system compared to the subcutaneous tissue. Typically, the intensity of the current delivered with a view to cardiac shutdown can range from 1 to 20 mA and the voltage delivered can range from 0.5 to 15 volts.

The one or more surgeons in charge of the operation are thus able to easily connect the electrode, typically the anode of the cardiac stimulator, to the accessory catheter, or to the conductive sleeve engaged around the accessory catheter, then to connect the other electrode as usual, typically the cathode, to the guidewire of the valve/stent/balloon assembly or of the assembly composed of valve and self-expanding stent.

Thus, the step for preparing for shutdown of the heart is simpler and quicker to carry out.

Moreover, the inventor considers that an accessory catheter according to the invention can reduce the risks of complications associated with the electrosystolic stimulation probes according to the prior art which are placed in the right ventricle.

The introducer or the delivery catheter can be introduced as usual by a transapical route or by a transfemoral route, the latter being preferred since it is less invasive for weakened patients.

The introducer or the delivery catheter can incorporate a peripheral perfusion system usually called a flush, which may be put in place in order to clear any possible blood clots from the interior of the introducer or of the catheter.

The artificial valve can be introduced and positioned in the artery by means of a conventional valve catheter, itself introduced into the introducer. The artificial valve then occupies a folded position and does not form an obstacle to the introduction and sliding of the valve catheter in the introducer and then in the artery, or in the delivery catheter and then in the artery.

Then, in the deployed position, the artificial valve bears against the outer wall of the native heart valve in place of the latter and crushes it.

A conventional valve catheter thus makes it possible to introduce and position the artificial valve at the suitable location, in the same operating maneuver as the one carried out for opening and crushing the native valve. After opening and crushing of the latter, the valve catheter is slid axially in the distal direction in order to bring the artificial valve to the suitable location in the aperture of the native valve.

During the opening and crushing of the native valve, and thereafter, the one or more surgeons operating on the patient apply a cardiac stimulation by means of the external cardiac stimulator, the electrical current circulating between the cathode and the anode of the stimulator, the cathode being connected to the guidewire of the artificial valve and the anode being connected to the conductive element of the peripheral venous catheter according to the invention, in contact with the subcutaneous tissue of the patient or with the inner wall of a peripheral vein.

Simultaneously with the ventricular stimulation, the artificial valve is deployed. The valve catheter is then withdrawn.

The same steps can be performed for all types of peripheral vascular interventions.

Thus, the invention also relates to a method for placement of a cardiac, aortic or arterial implant, comprising the following steps:

a/ introduction of an introducer and/or of a delivery catheter by a percutaneous route or into a peripheral artery of a human body;

b/ introduction of a guidewire into the tubular sheath of the introducer or of the delivery catheter, for advancing a cardiac, aortic or arterial implant;

c/ introduction of an accessory catheter into a peripheral vein or artery of the human body, the accessory catheter comprising at least one tubular insertion sheath and at least one electrically conductive element, of which a distal portion is exposed on at least one part of the outer periphery of the sheath, or the accessory catheter comprising a sleeve made of electrically conductive material on at least one part of its periphery;

d/ connection between one of the two electrodes of an external cardiac stimulator and the accessory catheter, or the sleeve engaged around the accessory catheter, and connection between the other of the two electrodes of the cardiac stimulator and the guidewire;

e/ placement of the implant;

g/ before, during or after the step, cardiac shutdown by means of the external cardiac stimulator.

Generally, the invention relates to the use of a cutaneous or subcutaneous or endovascular peripheral anode making it possible, by way of a metal guide positioned in the heart, to convey the electric current as far as the heart and thus stimulate the latter at a variable frequency, typically between 40 and 220 beats per minute, in order to temporarily stabilize it by shutting it down or to drive it in cases of bradycardia or other electrical conduction disturbances stopping or slowing down the heart rate during an infarct or a coronary, valvular or peripheral arterial intervention.

The endovascular anode can be situated anywhere on the arterial or venous circulatory system.

The voltage applied in order to obtain the cardiac shutdown is preferably between 0.5 and 15 V. The current applied is advantageously between 1 and 20 mA.

The characteristic impedance is preferably between 300 and 700 ohms.

For an operation for placement of percutaneous valves or aortic endoprostheses (TEVAR) or balloon angioplasties of aortic constrictions (coarctations of the aorta), the heart rate to be obtained by the cardiac shutdown according to the invention is advantageously between 140 and 220 beats per minute.

For a coronary application, in the case of use of an angioplasty tool such as the Rotablator® for example, or in the management of infarcts with conduction disturbances or for the treatment of peripheral arteries such as the carotid arteries (vectors of cardiac slow-down by receptor stimulation around the carotid glomus), the rate is advantageously between 50 and 100 beats per minute.

In summary, the advantages of an assembly according to the invention repeat those of an assembly according to WO2016/162315 A1, which can be enumerated as follows:

- simpler and quicker placement of an electrode, typically the ventricular stimulation anode, during the operation for replacement of a defective aortic valve or the operation for placement of any aortic or arterial implant (thoracic aortic endoprosthesis, stent);
- no need to insert an additional subcutaneous needle as support for an electrode, typically the anode, for the cardiac stimulator;
- reduced time and costs of the operation for replacement of a defective cardiac valve or of the operation for placement of any aortic or arterial implant (thoracic aortic endoprosthesis, stent);
- increased efficacy of the temporary stimulation with a view to performing the desired cardiac shutdown, on account of the lower impedance of the vascular system encountered by the electrical stimulation current since the sleeve around an accessory venous catheter is directly in contact with said system, in contrast to the needles of the prior art which come into contact with the cutaneous tissue of a patient, which necessarily has a higher impedance;
- increased efficacy of the temporary stimulation with a view to performing the desired cardiac shutdown on account of the stability of the rigid guide (diameter of the order of 1.455 mm) in the left ventricle, instead of the instability of the electrosystolic probe according to the prior art placed in the right ventricle;
- the possibility of performing the temporary cardiac stimulation with a lower electric current on account of the lower impedance of the vascular system encountered between the two electrodes of the external stimulator;
- the elimination of the risks of complications associated with the temporary stimulation probes according to the prior art which are placed in the right ventricle;
- the possible use of the introducer or of the delivery catheter for several different types of TAVI interventions such as replacement of an aortic valve, pulmonary valve, tricuspid valve or mitral valve. In particular, for replacement of a degenerated tricuspid valve, only the technique of introducing a stimulation probe into the right ventricle by means of the guide rail (diameter 0.89 mm) is conceivable, since it is inconceivable to place both the guide rail and an electrosystolic probe because the expansion of the balloon or of the valve prosthesis would compress the probe, with the inherent risk of interrupting the stimulation or of wedging the stimulation probe;

the possible use in the pediatric population during procedures performed on the valves or hearts which present greater tachycardia and are more mobile than in the adult population. Moreover, this is a population in which femoral venous puncture may be very difficult, likewise the placement of a stimulation probe in the right ventricle. Finally, the walls of the right ventricle in infants are thin and fragile, thereby increasing the risk of serious complications such as tamponade. This is also the population described in publication [2];

the possible use for all types of peripheral vascular interventions.

In addition, compared to an assembly according to the application WO2016/162315 A1, an assembly according to the invention has the following additional advantages:

no modification of the protocol, since the introduction of the accessory (peripheral venous or arterial) catheter according to the invention remains the same as for the existing accessory catheters. This operation is very simple and easy to use and may readily be performed by an assistant or nurse who does not need to have any particular training to perform this task.

increased safety of a TAVI intervention or any other type of cardiac intervention (mitral valve, tricuspid valve) or any type of peripheral vascular intervention, since the (accessory) peripheral catheter is withdrawn last during the procedure. With the accessory catheter and therefore the connection to the cardiac stimulator installed at the very last moment, cardiac stimulation can be initiated even in an emergency situation;

possibility of using any type of TAVI delivery catheter or introducer or any other type of heart valve or those intended for existing peripheral vascular interventions, since the stimulation electrodes connected respectively to the guidewire and to the arterial or venous catheter do not in any way impact the choice of the delivery catheter or introducer used in the TAVI.

The invention further relates to the use of the assembly with introducer or delivery catheter, and with a peripheral venous catheter previously described, for the replacement of an aortic, pulmonary, tricuspid or mitral valve, or for the placement of a thoracic aortic endoprosthesis or a carotid stent.

DETAILED DESCRIPTION

Other advantages and features of the invention will become clearer on reading the detailed description of the invention, which is given by way of a non-limiting example and with reference to the accompanying figures, in which.

In the description below, and in the whole of the present application, the terms "distal" and "proximal" are used with reference to the body of a patient whose defective native aortic valve is replaced by an artificial aortic valve. Thus, the distal end of an introducer is the end situated farthest inside the patient during the operation for replacement.

To simplify matters, the same elements in an assembly according to the invention and in an assembly according to the prior art are designated by the same references.

It should be noted that the various elements are not necessarily shown to scale.

Figure 1:
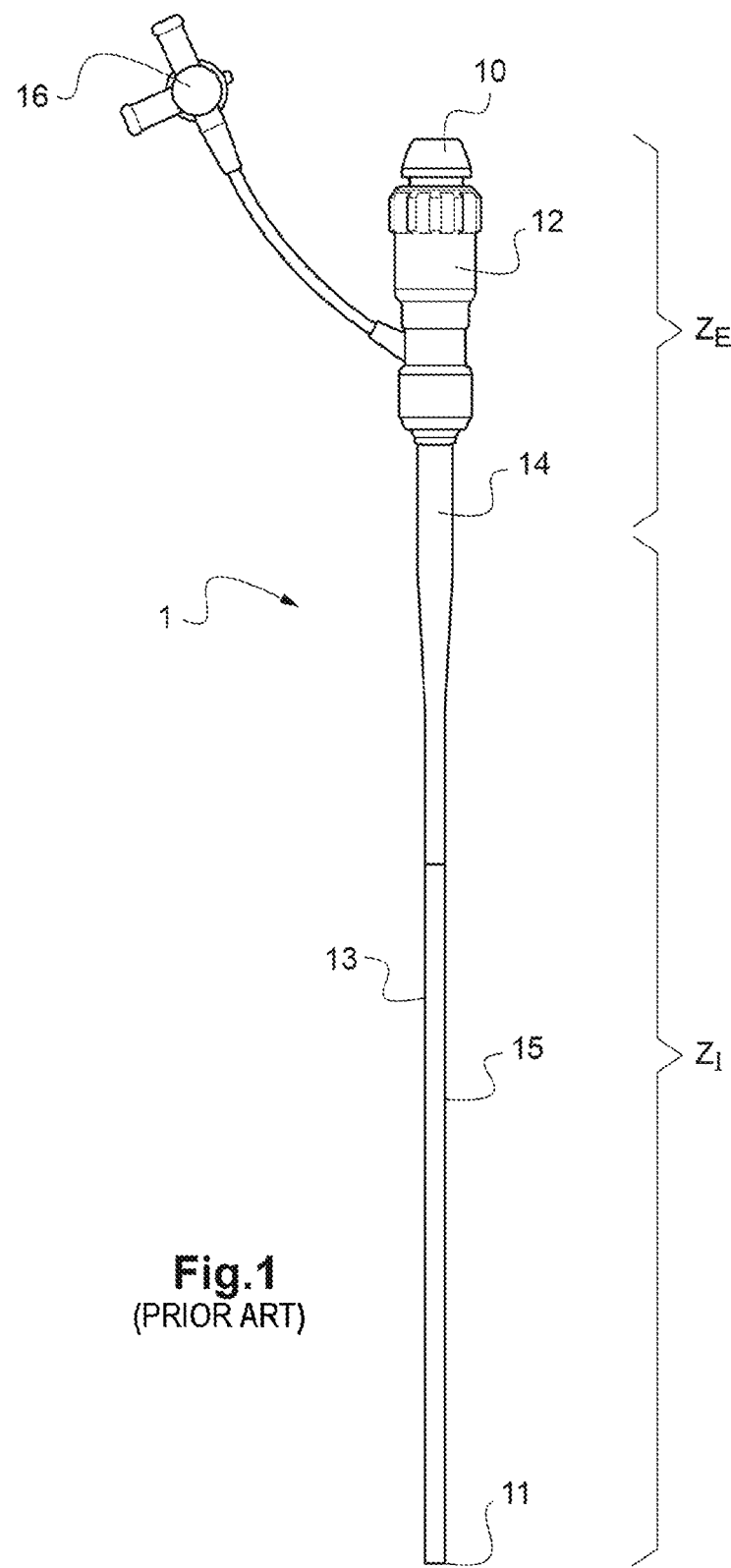
FIG. 1 is a perspective view of an introducer according to the prior art, intended to be introduced into a femoral artery in the groin region of a patient.

FIG. 1 shows an introducer 1 for replacing a heart valve by a transfemoral route.

Between its proximal end 10 and its distal end 11, this introducer 1 of generally tubular shape comprises a nozzle 12 which is continued by at least one outer tubular sheath 13 formed of two tubular portions 14, 15, from proximal to distal, considered with respect to the introduction into a femoral artery of a patient on whom an operation is to be performed, that is to say from the top downward in FIG. 1.

The nozzle 12 generally incorporates within it a set of leaktight valves to provide hemostasis, that is to say to ensure that the blood is retained inside the patient's blood vessels during the intervention.

The tubular sheath 13 may be extensible or non-extensible in order to permit the passage of a surgical intervention device such as a valve catheter, as is explained below. The material from which the sheath 13 is made is a biocompatible material such as silicone. It may also be made of Teflon® or of polyurethane. The sheath may advantageously be covered on the outside with a hydrophilic layer and on the inside with a layer having a low coefficient of friction in order to facilitate the sliding of an intervention device.

The introducer 1 illustrated in FIG. 1 likewise comprises an integrated rinsing device 16 with faucets, commonly referred to as a flush, for rinsing the inside of the introducer 1 by means of a suitable rinsing liquid.

All the elements of the introducer 1 that are present in the proximal or outer zone $Z_E$ are intended to remain outside the patient's body, while the entire distal portion 15 of the sheath 13 defining the distal zone $Z_1$ is intended to be introduced into a femoral artery of the patient.

The introducer 1 illustrated is, for example, the one sold commercially under the trade name "Edwards eSheath introducer set", which is sold commercially by Edwards Lifesciences.

Figure 2A:
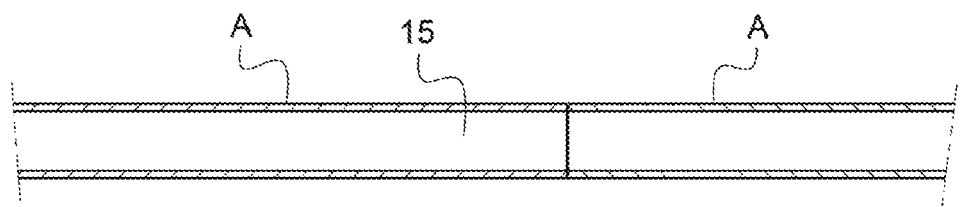
FIGS. 2A to 2C show, in partial longitudinal sectional views, various steps involved in sliding a valve catheter into the introducer according to FIG. 1, in order to fit an artificial valve in place as a replacement for a defective native aortic valve.
Figure 2B:
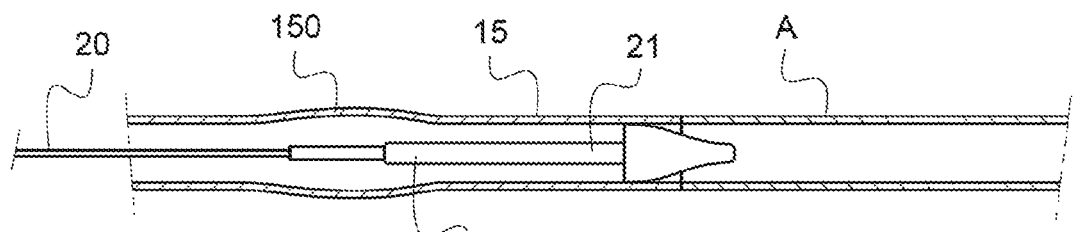
Figure 2C:
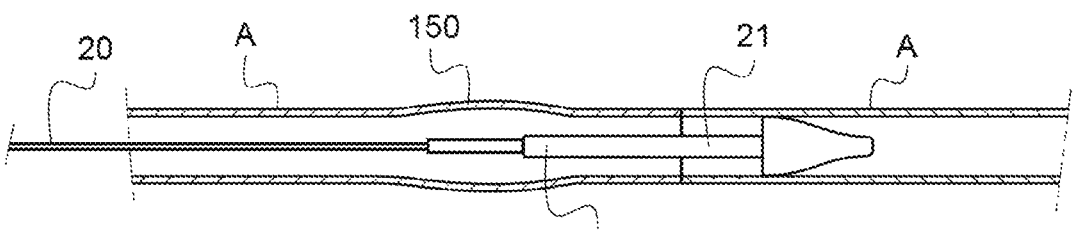

FIGS. 2A to 2C show the advance of a valve catheter 2, composed of a guidewire 20 and of an assembly 21 formed by an artificial valve fixed to a radial expansion stent and an inflatable balloon for effecting this expansion, inside the distal portion 14 of the tubular sheath of the introducer 1 already introduced into a femoral artery A.

The tip of the assembly 21 makes it possible to easily penetrate the deficient native aortic valve.

It will be seen from these figures that, the further the valve catheter 2 slides, the portion 15 of the tubular sheath temporarily deforms radially to form a slight protuberance 150. When the tubular sheath is not extensible, it does not deform radially.

Figure 3:
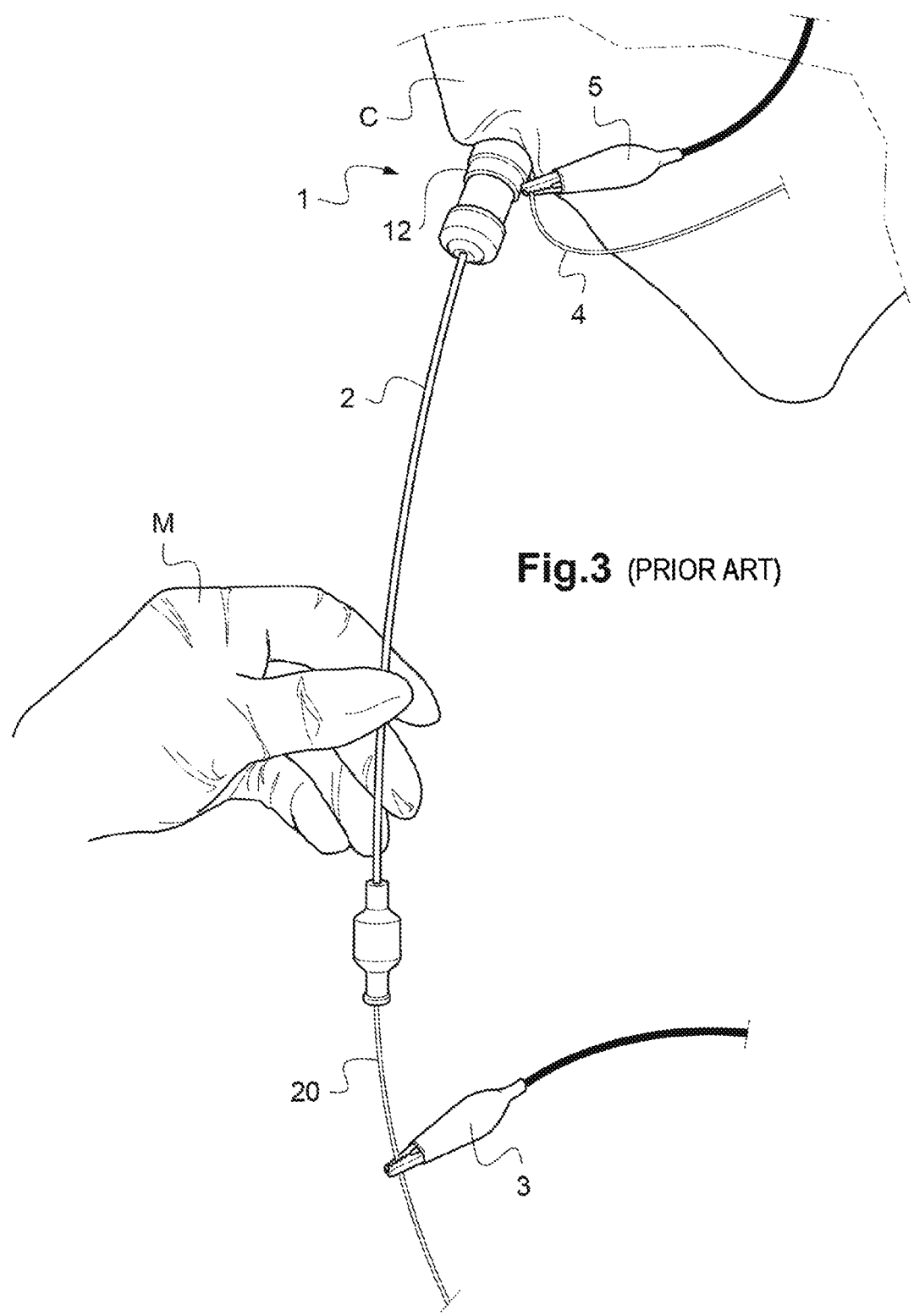
FIG. 3 shows, in a schematic perspective view from outside a patient, the step involving the placement of a valve catheter and of the cardiac stimulation electrodes according to the prior art.

It will be seen from FIG. 3 that the hand M of a surgeon introduces the valve catheter 2 into the introducer 1 already introduced into the femoral artery of a patient, with the nozzle 12 protruding outside of the body C.

This introduction of the valve catheter 2 allows the assembly 21 to be brought to the level of the deficient calcified aortic valve that is to be replaced.

Normally, as is likewise shown in FIG. 3, a clip 3 known as a crocodile clip is fixed by being clipped onto the guidewire 20 of the valve catheter 2. This clip 3 is connected to the cathode of a cardiac stimulator (not shown) situated outside of the body C.

A needle (not shown) is likewise inserted into the subcutaneous tissues of the body C of the patient on whom a procedure is to be performed. A metal wire 4 is fixed on this needle.

A crocodile clip 5 is likewise fixed by being clipped onto the metal wire 4.

This clip 5 is connected to the anode of the cardiac stimulator outside the body.

Thus, when the artificial valve is at the level of the natural aortic valve that is to be replaced, and before putting the artificial valve itself into place, i.e. before inflating the balloon and thus expanding the stent to which the valve is fixed, the surgeon first of all effects rapid ventricular stimulation of the left ventricle.

To do this, an electrical signal is delivered between the cathode and the anode by way of the clips 3 and 5, with the balloon serving as electrical insulator between these two electrodes.

Figure 4:
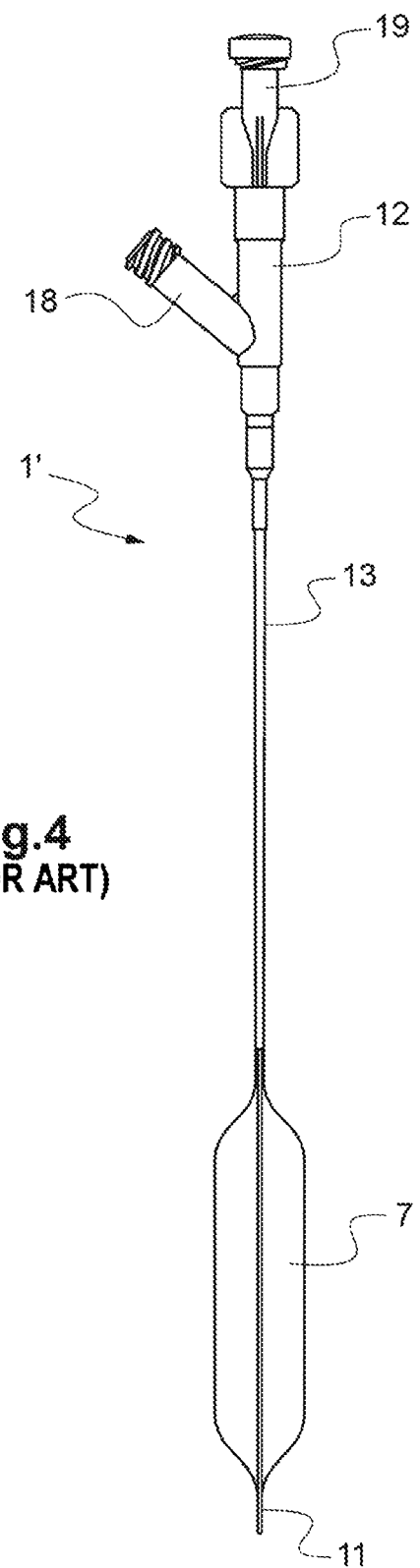
FIG. 4 is a schematic perspective view of a delivery catheter according to the prior art, intended to be introduced directly into the artery of a patient without the need for an introducer.

FIG. 4 illustrates a delivery catheter 1' which may be introduced directly into the artery of a patient without the need for an introducer. More precisely, the catheter 1' comprises a nozzle 12, which is continued by an insertion sheath 13. The nozzle 12 comprises a port 18 for inflation/deflation of a balloon 7 at the distal end 11, which makes it possible to expand a prosthetic valve (not shown).

Faced with numerous operations for replacing an aortic valve via a femoral route of the kind that has been briefly described, and in particular faced with the precise and delicate placement of the additional supplementary needle, and also the placement and retention of the connecting crocodile clips on two spaced-apart supports, the inventor of the present invention has thought to integrate the metal wire 4 directly in an introducer 1 or in a delivery catheter 1'. This solution is described and claimed in the patent application WO2016/162315 A1.

Although this solution affords many advantages compared to the technique according to the prior art, it nonetheless has an important disadvantage, namely that of requiring the production of specific introducers or delivery catheters.

Thus, the inventor has first considered integrating the function of the metal wire not in a specific introducer or delivery catheter but instead in an existing peripheral venous catheter 1".

Such a venous catheter 1" can be of a small diameter, typically 2 mm or less, and of a short length. It meets the standards applying to peripheral intravascular catheters. It will be recalled here that the primary function of a peripheral venous catheter is to deliver a liquid for rehydration of the patient, a drug treatment or a transfusion.

More particularly, in the context of a TAVI, the arterial catheter 1" makes it possible to perform a control angiography, on the one hand in order to check the positioning of the prosthetic aortic valve, and on the other hand in order to verify the absence of complications, in particular of vascular complications, or even to manage them. (The primary function of a peripheral venous catheter is to deliver a liquid for rehydration of the patient, a drug treatment or a transfusion).

According to the invention, the insertion sheath of a peripheral arterial catheter 1" incorporates at the periphery a wire or an electrically conductive band of very small thickness, typically of the order of a millimeter or less, which adds only a little thickness to a conventional venous catheter sheath and therefore does not impede the advance of the latter during its introduction into an artery or peripheral vein V.

In practice, a surgeon or interventionalist seeking to perform an operation for replacement of a cardiac stimulation valve, with cardiac stimulation concomitant with the placement of the prosthetic valve, begins by positioning the peripheral venous or arterial catheter 1" in such a way that the conductive element of its sheath will touch either a subcutaneous zone of the patient or the wall of the peripheral vein or artery of the patient.

Once this positioning has been carried out, the introducer 1 or the delivery catheter 1' can be introduced in the usual way by the surgeon.

Once the positioning of the introducer 1 or of the catheter 1' in the femoral artery A has been completed, the electrical connection 6 can be connected directly to the anode of an external cardiac stimulator 9 by way of a connection wire 90.

Usually, a clip such as the crocodile clip 3 shown in FIG. 3 can in turn be fixed by clipping it to the guidewire 20 of an introducer 1 or of a valve catheter 1'. This clip is connected to the cathode of the external cardiac stimulator by way of a connection wire 91.

Thus, the temporary cardiac stimulation for performing the desired cardiac shutdown can take place between the cathode, connected electrically to the guidewire 20, and the anode, connected electrically to the electrically conductive element of the peripheral venous catheter 1".

Figure 5:
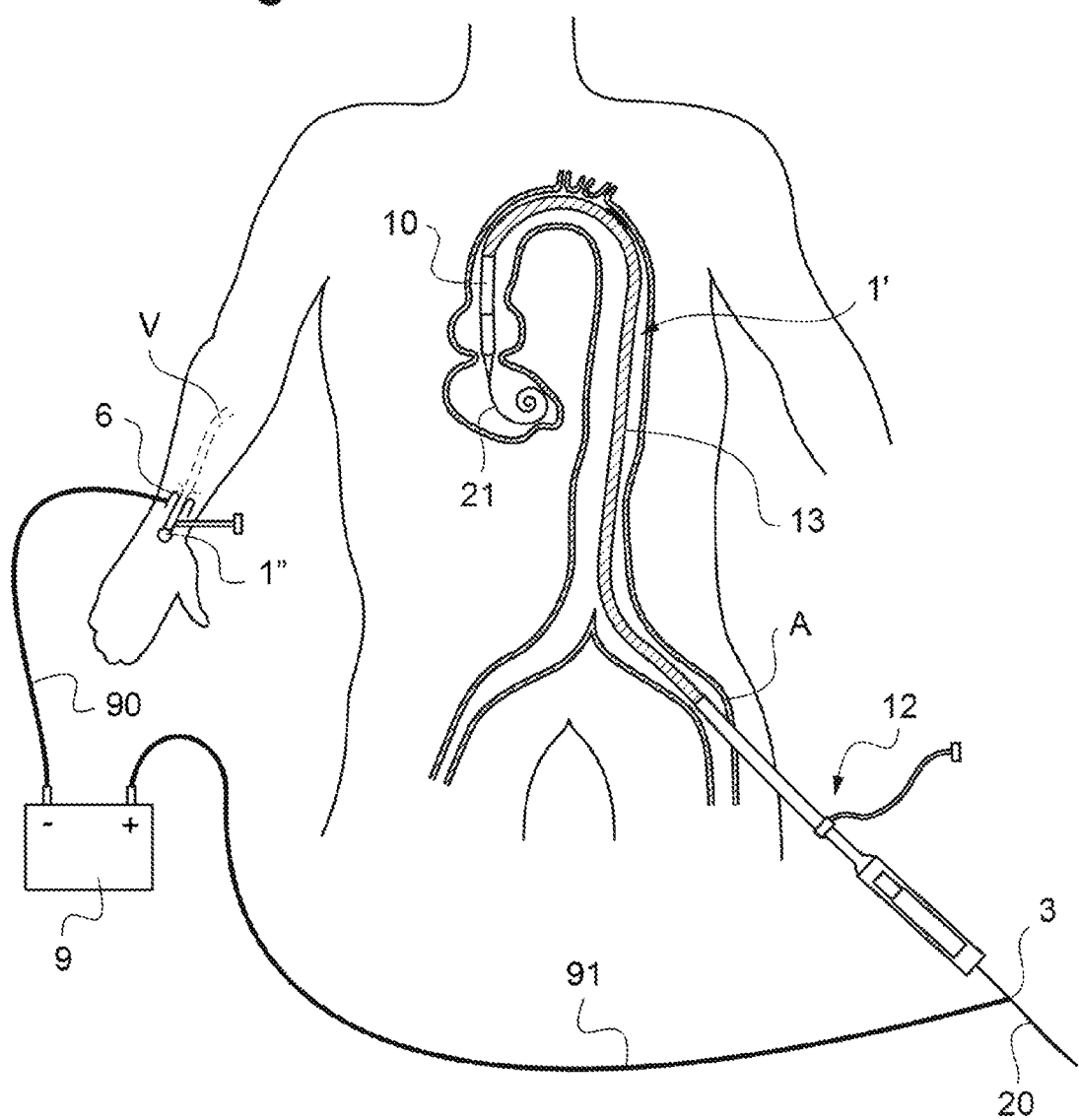
FIG. 5 illustrates schematically the use of an assembly according to the invention with a venous catheter according to the invention and with a prosthetic valve delivery catheter introduced directly into an artery of a patient.

FIG. 5 provides a schematic view of all the elements in question, namely the use of an assembly with delivery catheter 1' for the delivery of a prosthetic valve 10 through the aortic arch of a patient and with a peripheral venous catheter 1" according to the invention.

As can be seen in FIG. 5, the catheter 1' is introduced from the femoral artery and a guidewire 20 is introduced directly into the delivery catheter 1'. The distal end 21 of the guidewire 20 winds up on itself when coming into contact with the endothelium of the left ventricle of the patient. This distal end 21 of the guidewire 20 at all times ensures the electrical contact and therefore the passage of the current from the cathode of the external cardiac stimulator 9 via the electrical connection wire 91.

The passage of the current to the anode of the cardiac stimulator 9 is for its part ensured by the conductive sheath of the peripheral venous catheter 1" and therefore in contact with the subcutaneous tissue of the patient or the peripheral vein and connected moreover to the electrical connection wire 90.

The invention is not limited to the examples that have just been described; it is in particular possible to combine features of the examples illustrated within variants that are not illustrated.

Other variants and improvements may be contemplated without thereby departing from the scope of the invention.

CITED REFERENCES

[1]: «*Registry of Transcatheter Aortic-Valve Implantation in High-Risk Patients*», Gilard et al; the New England Journal of Medicine: pp 1705-1715

[2]: «*Left Ventricular Guidewire Pacing to Simplify Aortic Balloon Valvuloplasty*», Susanne Navarini et al; Catheterization and Cardiovascular Interventions 73: pp 426-427 (2009)

[3]: «*A novel Approach for Transcoronary Pacing in a Porcine Model*», Roland Prodzinsky et al; Journal of Invasive Cardiology 24(9): pp 451-455 (2012)

[4]: «*Optimizing of Transcoronary Pacing in a Porcine Model*», Konstantin M. Heinroth, et al, Journal of Invasive Cardiology 21, pp 634-638 (2009)

The invention claimed is:

1. An assembly for placement of a cardiac, aortic or arterial implant, comprising:
   a device forming an introducer or a valve delivery catheter comprising at least one tubular insertion sheath, intended to be introduced into an artery of a human body;
   an accessory catheter intended to be introduced into a peripheral vein or artery of the human body;
   a sleeve adapted to be engaged around the accessory catheter, the sleeve being made of electrically conductive material over at least part of its outer periphery, such that, when the accessory catheter is introduced into the peripheral vein or artery of the human body, the conductive periphery of the sleeve is in contact with the subcutaneous tissue of the body or with the wall of the artery or of the vein, the sleeve additionally comprising an electrical connection to an electrode of a cardiac stimulator outside the body;
   a guidewire intended to be introduced into the tubular sheath of the introducer or of the delivery catheter for advancing the implant, the guidewire comprising a metal part additionally serving as a connection to the other electrode of the external cardiac stimulator.

2. The assembly as claimed in claim 1, the electrode of the cardiac stimulator connected to the electrically conductive sleeve engaged around the insertion sheath of the accessory catheter being the anode, while the one connected to the metal part of the guidewire introduced into the introducer or the delivery catheter is the cathode.

3. The assembly as claimed in claim 1, in which the electrically conductive sleeve is formed as one piece made of conductive material, for example carbon.

4. The assembly as claimed in claim 3, the sleeve being formed by a sheath comprising on its outer periphery an electrically conductive coating.

5. The assembly as claimed in claim 3, the sleeve being elastic so as to be able to engage on peripheral venous or arterial catheter sheaths of different diameters, typically external diameters of between 0.2 and 2.2 mm.

6. The assembly as claimed in claim 1, constituting an assembly for replacement of a cardiac valve by a percutaneous route, the guidewire being adapted for the advance of an artificial valve intended to replace the cardiac valve.

7. An assembly for placement of a cardiac, aortic or arterial implant, comprising:
   a device forming an introducer or a valve delivery catheter comprising at least one tubular insertion sheath, intended to be introduced into an artery of a human body;
   an accessory catheter, intended to be introduced into a peripheral vein or artery of the human body, the accessory catheter comprising at least one tubular insertion sheath and at least one electrically conductive element, of which a distal portion is exposed on at least one part of the outer periphery of the sheath in such a way as to be in contact with the subcutaneous tissue of the body or with the peripheral vein or artery, and of which a proximal portion, accessible from the outside of the body, comprises an electrical connection so as to serve as a connection to an electrode of a cardiac stimulator outside the body;
   a guidewire intended to be introduced into the tubular sheath of the introducer or of the delivery catheter for advancing the implant, the guidewire comprising a metal part additionally serving as a connection to the other electrode of the external cardiac stimulator.

8. The assembly as claimed in claim 7, the electrode of the cardiac stimulator connected to the accessory catheter being the anode, while the one connected to the metal part of the guidewire inserted into the introducer or the delivery catheter is the cathode.

9. The assembly as claimed in claim 7, in which the electrically conductive element of the accessory catheter is a wire or a metal band housed at least partially within the thickness of the sheath, of which a distal portion is exposed at the outer periphery of the sheath.

10. The assembly as claimed in claim 9, the cross section of the wire or of the metal band being between 0.25 and 5 mm$^2$.

11. An assembly for placement of a cardiac, aortic or arterial implant, comprising:
    a device forming an introducer or a valve delivery catheter comprising at least one tubular insertion sheath, intended to be introduced into an artery of a human body;
    an accessory catheter intended to be introduced into a peripheral vein or artery of the human body;
    a sleeve adapted to be engaged around the accessory catheter, the sleeve being made of electrically conductive material over at least part of its outer periphery, such that, when the accessory catheter is introduced into the peripheral vein or artery of the human body, the conductive periphery of the sleeve is in contact with the subcutaneous tissue of the body or with the wall of the artery or of the vein, the sleeve additionally comprising an electrical connection to an electrode of a cardiac stimulator outside the body;
    a guidewire intended to be introduced into the tubular sheath of the introducer or of the delivery catheter for advancing the implant, the guidewire comprising a metal part additionally serving as a connection to the other electrode of the external cardiac stimulator;
    wherein said assembly constitutes an assembly for placement of an aortic endoprosthesis or carotid stent, the guidewire being adapted for the advance of the endoprosthesis or stent, or the guidewire being independent of the one which delivers the prosthesis or the balloon but which is coupled to another guidewire in contact with the patient's heart.

12. An assembly for placement of a cardiac, aortic or arterial implant, comprising:
- a device forming an introducer or a valve delivery catheter comprising at least one tubular insertion sheath, intended to be introduced into an artery of a human body;
- an accessory catheter, intended to be introduced into a peripheral vein or artery of the human body, the accessory catheter comprising at least one tubular insertion sheath and at least one electrically conductive element, of which a distal portion is exposed on at least one part of the outer periphery of the sheath in such a way as to be in contact with the subcutaneous tissue of the body or with the peripheral vein or artery, and of which a proximal portion, accessible from the outside of the body, comprises an electrical connection so as to serve as a connection to an electrode of a cardiac stimulator outside the body;
- a guidewire intended to be introduced into the tubular sheath of the introducer or of the delivery catheter for advancing the implant, the guidewire comprising a metal part additionally serving as a connection to the other electrode of the external cardiac stimulator, wherein said assembly constitutes an assembly for placement of an aortic endoprosthesis or carotid stent, the guidewire being adapted for the advance of the endoprosthesis or stent, or the guidewire being independent of the one which delivers the prosthesis or the balloon but which is coupled to another guidewire in contact with the patient's heart.

* * * * *